(12) United States Patent
Chiu

(10) Patent No.: US 6,875,287 B2
(45) Date of Patent: Apr. 5, 2005

(54) WATER RECLAMATION RATE IN SEMICONDUCTOR FABRICATION WET BENCHES

(75) Inventor: Cheng-Tsung Chiu, Hsinchu (TW)

(73) Assignee: Mosel Vitelic, Inc. (TW)

(*) Notice: Subject to any disclaimer, the term of this patent is extended or adjusted under 35 U.S.C. 154(b) by 443 days.

(21) Appl. No.: 10/093,226

(22) Filed: Mar. 5, 2002

(65) Prior Publication Data

US 2002/0124869 A1 Sep. 12, 2002

(30) Foreign Application Priority Data

Mar. 6, 2001 (TW) .......................................... 90105154 A

(51) Int. Cl.[7] ................................................. C23G 1/36
(52) U.S. Cl. .............................. 134/10; 134/18; 137/2; 137/5; 210/739; 210/746
(58) Field of Search ........................ 134/10, 18; 137/2, 137/5, 119.01; 210/739, 746, 96.1

(56) References Cited

U.S. PATENT DOCUMENTS 6,178,975 B1    1/2001  Aoki
6,379,548 B1 *  4/2002  Kurokawa et al. .......... 210/631
6,622,745 B1 *  9/2003  Smith et al. .................. 137/2

OTHER PUBLICATIONS

R.Donovan et al. Design of Recycling System for Spent Rinse Water from Sandia's Microelectronics Development Laboratory (MDL). Jan. 19, 2001. http://www.sandia.gov/aqua/Papers/balazs3.pdf.*

* cited by examiner

Primary Examiner—M. Kornakov
(74) Attorney, Agent, or Firm—Townsend and Townsend and Crew LLP

(57) ABSTRACT

Embodiments of the present invention are directed to improving the reclamation rate of the waste water of wet benches in semiconductor fabrication. In accordance with an aspect of the invention, a method for improvement of water reclamation rate comprises choosing a rinse recipe for a wet bench. The wet bench is activated, and waste water quality of waste water produced by the rinse recipe from the wet bench is detected to generate water quality data for a plurality of reclamation switch time levels. The waste water is directed to a water reclamation system during a reclamation time period after each of the plurality of reclamation switch time levels. The water quality data of the waste water is analyzed for the plurality of reclamation switch time levels. The method further comprises determining from analyzing the water quality data the best reclamation switch time for the chosen rinse recipe for the wet bench.

20 Claims, 4 Drawing Sheets

WATER RECLAMATION RATE IN SEMICONDUCTOR FABRICATION WET BENCHES

CROSS-REFERENCES TO RELATED APPLICATIONS

This application claims priority from R.O.C. Patent Application No. 090105154, filed Mar. 6, 2001, the entire disclosure of which is incorporated herein by reference.

BACKGROUND OF THE INVENTION

Water consumption in semiconductor fabrication is high, due largely to the substantial quantities of rinse water used on wet benches. Many chemical reagents and acidic solvents, such as $H_2SO_4$, HF or $H_3PO_4$, are used during the manufacturing process. Wet stations or wet benches are designed to remove chemical residue on the surface of wafers with deionized water.

Due to the wet bench's heavy water consumption, there is typically a reclamation system present designed to regenerate clean water from waste water discharged by the wet bench. Conventionally, the reclamation switch time of the wet bench is based on loose factory settings such as, for example: 200 seconds. When the wet bench is set to run a rinse recipe (e.g., Quick-Dump-Rinse (QDR) for 5 minutes), the waste water in the first 200 seconds is discharged and then the waste water after 200 seconds is conducted into the reclamation system for further regeneration. However, the reclamation rate is typically only 30%.

If the reclamation switch time of the wet bench is shortened to, for example, 100 seconds, the waste water discharged by the wet bench after 100 seconds will be rejected by the reclamation system because the residue present will exceed the maximum tolerance, producing a reclamation rate of even lower than 30%.

BRIEF SUMMARY OF THE INVENTION

Embodiment of the present invention are directed to improving the reclamation rate of the waste water of wet benches in semiconductor fabrication. The invention does so by ascertaining the best reclamation switch time before a given rinse recipe runs. By varying the reclamation switch time and analyzing the water quality data of the waste water directed to the water reclamation system, one can determine the best reclamation switch time to achieve the best reclamation rate. In specific embodiments, the best reclamation switch time is the lowest time level at which the conductivity of the waste water is generally below a preset limit representing the maximum tolerance of the reclamation system. In this way, the rejection of the waste water by the reclamation system is minimized by keeping the conductivity generally below the maximum tolerance of the reclamation system, and the reclamation period is maximized by selecting the lowest reclamation switch time level at which the conductivity is generally below the maximum tolerance of the reclamation system. The best reclamation switch time is then set as the default value for the wet bench.

In accordance with an aspect of the present invention, a method for improvement of water reclamation rate in a semiconductor fabrication wet bench comprises choosing a rinse recipe for a wet bench. The wet bench is activated, and waste water quality of waste water produced by the rinse recipe from the wet bench is detected to generate water quality data for a plurality of reclamation switch time levels. The waste water is directed to a water reclamation system during a reclamation time period after each of the plurality of reclamation switch time levels. The water quality data of the waste water is analyzed for the plurality of reclamation switch time levels. The method further comprises determining from analyzing the water quality data the best reclamation switch time for the chosen rinse recipe for the wet bench.

In some embodiments, the water quality data is collected by a data recorder. The rinse recipe may comprise a quick-dump rinse recipe, an overflow rinse recipe, or a final-rinse recipe. The waste water quality may comprise conductivity of the waste water.

In specific embodiments, the water quality data is analyzed by a computer to produce a plurality of water quality curves of the waster water. Each water quality curve corresponds to one of the reclamation switch time levels. The waste water quality comprises conductivity of the waste water. The best reclamation switch time is determined by selecting the lowest reclamation switch time level at which the conductivity of the waste water directed to the water reclamation system is generally below a preset limit. In one example, the preset limit is about 1000 $\mu$s/cm. The best reclamation switch time is determined by selecting the lowest reclamation switch time level at which the conductivity of the waste water is below the preset limit over, for instance, at least about 90%, more desirably at least about 95%, of the reclamation time period.

In accordance with another aspect of the present invention, a method for improvement of water reclamation rate in semiconductor fabrication wet benches comprises choosing a rinse recipe and setting a reclamation switch time for a wet bench. The wet bench is activated, and waste water quality of waste water produced by the rinse recipe from the wet bench is detected to generate water quality data. The method further comprises resetting the reclamation switch time for the wet bench and repeating the step of activating the wet bench and detecting the waste water quality of the waste water to generate corresponding water quality data for each of a plurality of reclamation switch time levels. The water quality data is analyzed for the plurality of reclamation switch time levels to obtain the best reclamation switch time.

In some embodiments, the water quality data is analyzed by a computer to produce a plurality of water quality curves of the waster water, each water quality curve corresponding to one of the reclamation switch time levels. The waste water quality comprises conductivity of the waste water. The waste water is directed to a water reclamation system during a reclamation period after each of the plurality of reclamation switch time levels. The best reclamation switch time is determined by selecting the lowest reclamation switch time level at which the conductivity of the waste water directed to the water reclamation system is generally below a preset limit.

DETAILED DESCRIPTION OF THE INVENTION

Embodiment of the present invention are directed to improving the reclamation rate of the waste water of wet benches in semiconductor fabrication. The best reclamation switch time is determined before a given rinse recipe runs. This is accomplished by varying the reclamation switch time and analyzing the water quality data of the waste water directed to the water reclamation system, and determining the best reclamation switch time to achieve the best reclamation rate.

Figure 1:
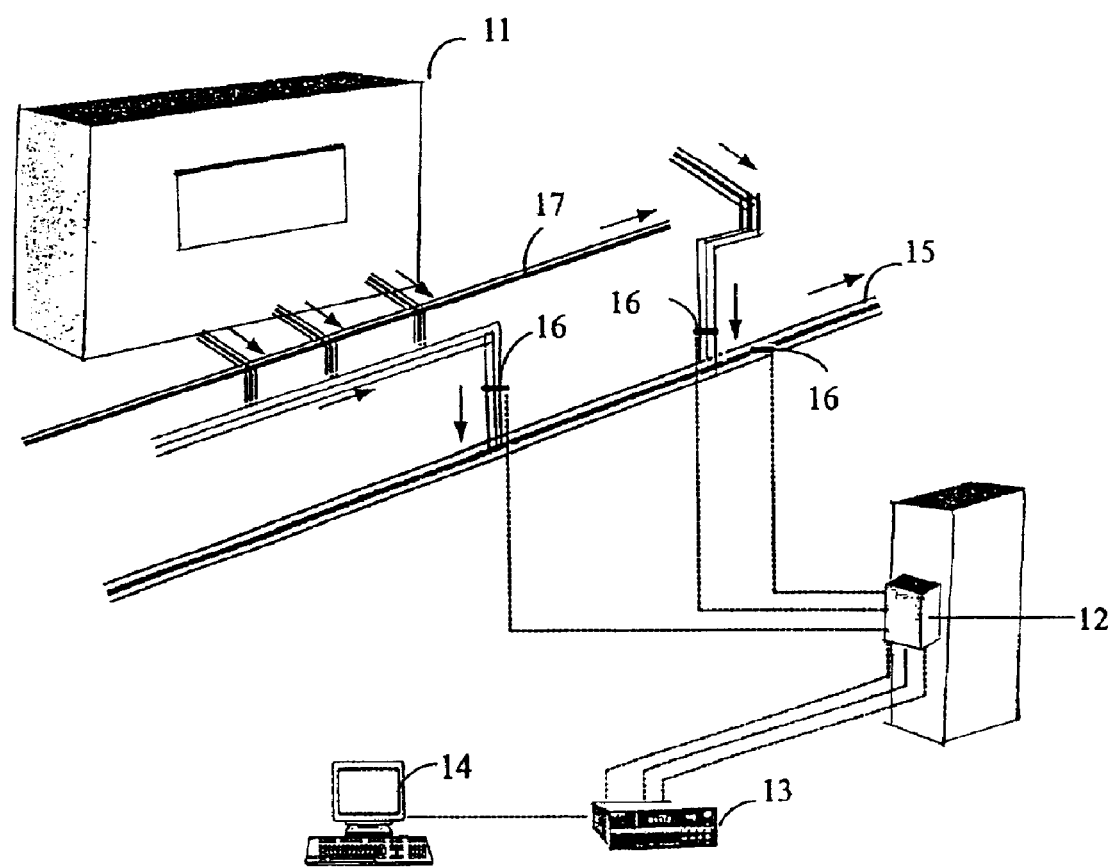
FIG. 1 is a schematic diagram which illustrates a system for improvement of the water reclamation rate in semiconductor wet benches according to an embodiment of the present invention.

In FIG. 1, there are two kinds of piping systems coupled to the wet bench 11. One is the reclamation line 15 for clean water regeneration, and the other is the waste water line 17 for water disposal. Waste water conducted into the reclamation line 15 is transported to the water reclamation system and the waste water conducted into the waste water line 17 for disposal. Conductivity meters 16 are coupled to the reclamation lines 15 to monitor the water quality according to the present invention. Characteristics detected by the conductivity meters 16 are collected by a recorder 13 which may be, for example, FLUKE 2640A. The data collected by the recorder 13 is further analyzed by a computer 14.

Figure 2:
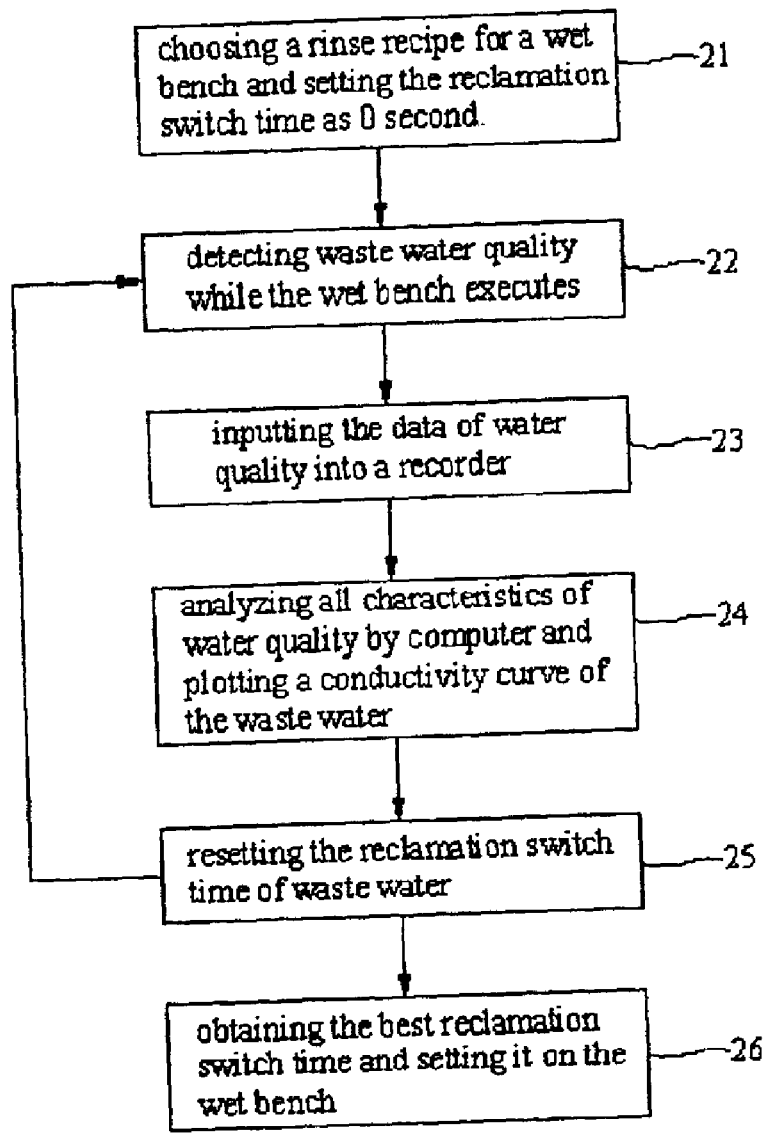
FIG. 2 is a flow chart illustrating the steps performed for improvement of water reclamation rate in semiconductor wet benches according to an embodiment of the invention.

In FIG. 2, a flow chart of steps performed for improvement of the water reclamation rate in semiconductor fabrication wet benches according to an embodiment is shown. In step 21, the rinse recipe of the wet bench 11 is chosen and the reclamation switch time is set as 0 second, which means all waste water discharged from the wet bench 11 is reclaimed into the reclamation line 15. A TEL wet bench is used here as an example.

There can be more than one water tank in one wet bench for rinsing or cooling. Some simple wet benches provide just one rinse recipe for one water tank, such as DNS or Sugai. There may be a plurality of preset rinse recipes provided in some kinds of wet benches for one water tank, such as TEL, or some may also provide manual setting of cleaning procedures. For example, the rinse recipe of the wet bench 11 (TEL) is set as post-SPM(9:1)QDR for processing with the sulfuric acid and hydrogen peroxide mixture ratio followed by the QDR process, and the reclamation switch time is 0 second, which means 100% of the waste water is reclaimed into the reclamation line 15. However, there are still other rinse recipes, such as Over-Flow Rinse (OFR) or Final-Rinse (FR), and the QDR is chosen here to illustrate the steps of water reclamation rate improvement.

Next, in step 22, when the rinse recipe post-SPM(9:1) QDR of the wet bench 11 is executed, the detection of waste water quality starts. Because all waste water is reclaimed, the water quality of all waste water is detected by the conductivity meters 16 coupled to the reclamation line 15. Next, characteristics of water quality are input into a recorder in step 23. The recorder, for example, FLUKE 2640A Recorder or others, can receive data input from at least one conductivity meter.

Next, in step 24, all water quality data is analyzed by a computer and plotted as a conductivity curve of the waste water.

Figure 3:
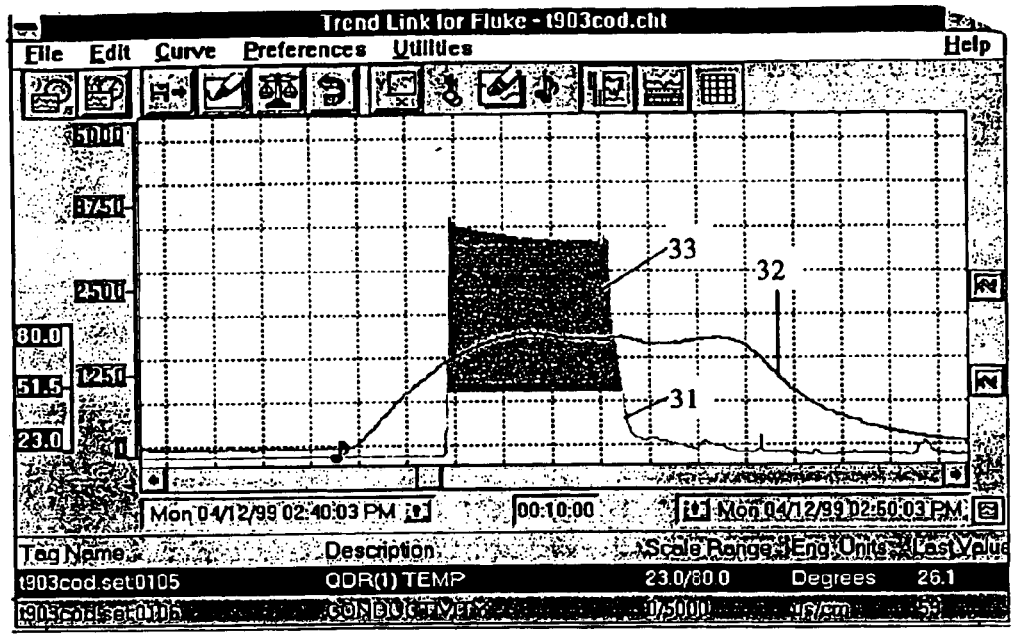
FIG. 3 is the conductivity curve in which the reclamation switch time is 0 second and all of the waste water is reclaimed in post-SPM(9:1)QDR for a specific example.

In FIG. 3, the conductivity curve of the 100% reclaimed waste water in QDR is shown. The vertical coordinate is the conductivity ($\mu$s/cm) of the waste water and the horizontal coordinate is the reclamation time period of the rinse recipe post-SPM(9:1)QDR. In FIG. 3, the gray line 31 is the conductivity change of the waste water, the black line 32 is the temperature (° C.) of waste water, and the gray area 33 is the time period during which the conductivity is greater than 1000 $\mu$s/cm. In this example, the maximum reclamation capacity of the waste water reclamation system is set as 1000 $\mu$s/cm. In FIG. 3, the reclamation time period of the gray area 33 is about 2 minutes, which means the waste water reclamation system in the fab will be overloaded in this condition.

Figure 4:
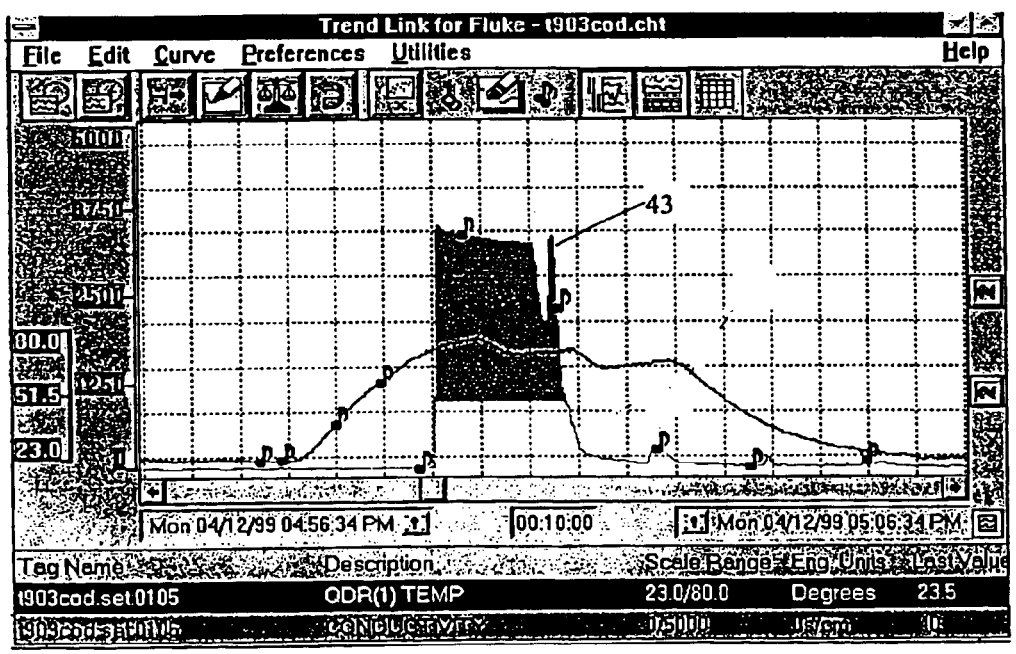
FIG. 4 is the conductivity curve in which the reclamation switch time is 30 second and the waste water is reclaimed after 30 seconds in post-SPM(9:1)QDR for the specific example.

Next, in step 25 as shown in FIG. 2, the reclamation switch time of waste water is reset. The reclamation switch time of waste water is set as 30 seconds while the rinse recipe of the wet bench 11 is still set as post-SPM(9:1)QDR. According to the setting, the wet bench 11 will run the rinse recipe post-SPM(9:1)QDR and the waste water will be discarded in the first 30 seconds and then reclaimed after 30 seconds. Steps 22–25 are repeated to obtain the results as plotted in FIG. 4. FIG. 4 shows the conductivity curve in which the reclamation switch time is 30 seconds and the waste water is reclaimed after 30 seconds in post-SPM(9:1) QDR. In FIG. 4, the reclamation time period of the gray area 43 is about 1.5 minutes, shorter than that in which the reclamation switch time is 0 seconds.

Figure 5:
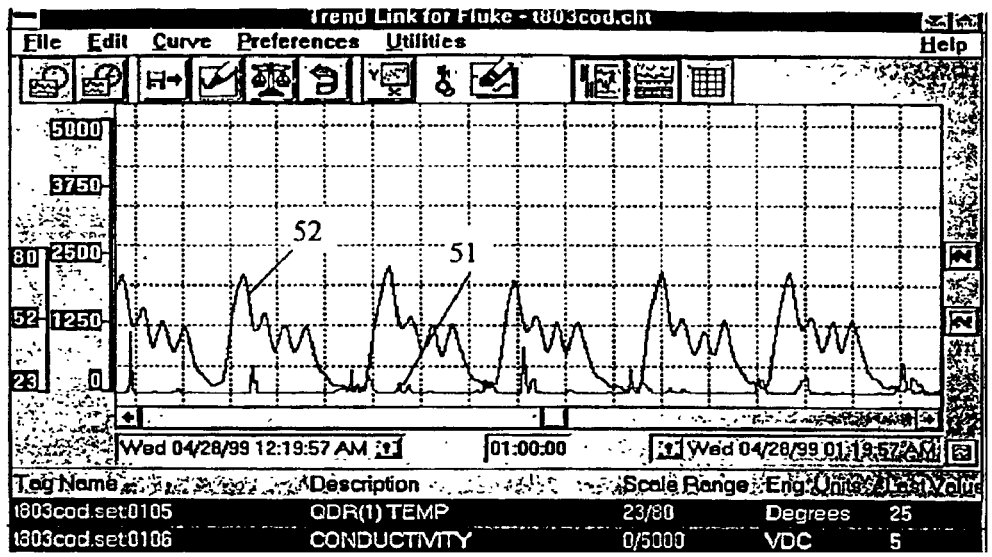
FIG. 5 is the conductivity curve in which the reclamation switch time is 105 seconds and the waste water is reclaimed after 105 seconds in post-SPM(9:1)QDR for the specific example.
Figure 6:
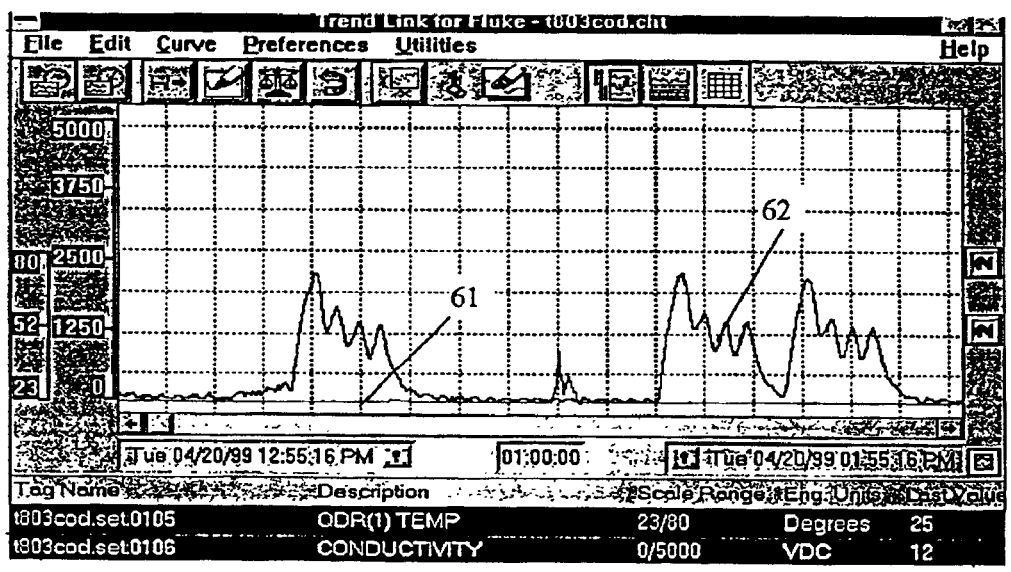
FIG. 6 is the conductivity curve in which the reclamation switch time is 200 seconds and the waste water is reclaimed after 200 seconds in post-SPM(9:1)QDR for the specific example.

The drain reclamation time is reset as 60, 75, 105, 115, and 200 seconds respectively and steps 22–25 are repeated to plot the conductivity curves. FIG. 5 is the conductivity curve in which the reclamation switch time is 105 seconds and the waste water is reclaimed after 105 seconds in post-SPM(9:1)QDR. When the drain reclamation time is set as 105 seconds, the gray line 51 is in excess of 1000 $\mu$s/cm over some time periods but only briefly. The gray line 51 is below the 1000 $\mu$s/cm limit over at least about 90%, more desirably at least about 95%, of the reclamation time period. FIG. 6 is the conductivity curve in which the reclamation switch time is 200 seconds and the waste water is reclaimed after 200 seconds in post-SPM(9:1)QDR. The factory setting of the reclamation switch time on the wet bench 11 is 200 seconds. When the waste water is reclaimed after 200 seconds, the conductivity gray line 61 is far below 1000 $\mu$s/cm, which means the reclamation switch time can be shortened.

The best reclamation switch time can be achieved by setting serial reclamation switch time and then recording the conductivity data of reclaimed waste water to monitor changes in water quality. If the conductivity of the reclaimed waste water is over the maximum value of the reclamation system in the fab, the reclamation system in the fab can be overloaded or will even reject the waste water for further processes. However, if too much waste water is discarded, the reclamation rate of waste water will be low.

After the wet bench 11 has run the drain recipe post-SPM (9:1)QDR in serial reclamation switch time (0, 30, 60, 75, 105, 115, and 200), 105 seconds is determined to be the best reclamation switch time for the wet bench 11 in running post-SPM(9:1)QDR process in this example. There are only a few sharp peaks shown after 105 seconds in excess of the limitation (1000 µs/cm) of the reclamation system, indicating only brief time periods of overloading. The conductivity of most waste water after 105 seconds is usually below 1000 µs/cm, which makes 105 seconds the best choice.

As a result, the best reclamation switch time is set as 105 seconds in step 26. When the wet bench is set to run post-SPM(9:1)QDR, the best water reclamation rate can be achieved by setting the rinse switch as 105 seconds thereafter.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A method for improvement of water reclamation rate in a semiconductor fabrication wet bench, the method comprising:
   choosing a rinse recipe specifying a type of rinse for a wet bench used to remove chemical residue on one or more wafer surfaces;
   activating the wet bench and detecting waste water quality of waste water produced by the rinse recipe from the wet bench to generate water quality data for a plurality of reclamation switch time levels, the waste water being directed to a water reclamation system during a reclamation time period after each of the plurality of reclamation switch time levels;
   analyzing the water quality data of the waste water for the plurality of reclamation switch time levels; and
   determining from analyzing the water quality data the best reclamation switch time for the chosen rinse recipe for the wet bench, wherein the waste water is to be discarded before reaching the reclamation switch time and to be reclaimed after reaching the reclamation switch time.

2. The method of claim 1 wherein the water quality data is collected by a data recorder.

3. The method of claim 1 wherein the rinse recipe comprises a quick-dump rinse recipe.

4. The method of claim 1 wherein the rinse recipe comprises an overflow rinse recipe.

5. The method of claim 1 wherein the rinse recipe comprises a final-rinse recipe.

6. The method of claim 1 wherein a parameter of the waste water quality to be detected comprises conductivity of the waste water.

7. The method of claim 1 wherein the water quality data is analyzed by a computer to produce a plurality of water quality curves of the waste water, each water quality curve corresponding to one of the reclamation switch time levels.

8. The method of claim 7 wherein a parameter of the waste water quality to be detected comprises conductivity of the waste water.

9. The method of claim 8 wherein the best reclamation switch time is determined by selecting the lowest reclamation switch time level at which the conductivity of the waste water directed to the water reclamation system is generally below a preset limit.

10. The method of claim 9 wherein the preset limit is about 1000 µs/cm.

11. The method of claim 9 wherein the best reclamation switch time is determined by selecting the lowest reclamation switch time level at which the conductivity of the waste water is below the preset limit over at least about 90% of the reclamation time period.

12. The method of claim 11 wherein the conductivity of the waste water is below the preset limit over at least about 95% of the reclamation time period.

13. A method for improvement of water reclamation rate in semiconductor fabrication wet benches, the method comprising:
   choosing a rinse recipe specifying a type of rinse and setting a reclamation switch time for a wet bench used to remove chemical residue on one or more wafer surfaces;
   activating the wet bench and detecting waste water quality of waste water produced by the rinse recipe from the wet bench to generate water quality data;
   resetting the reclamation switch time for the wet bench and repeating the step of activating the wet bench and detecting the waste water quality of the waste water to generate corresponding water quality data for each of a plurality of reclamation switch time levels; and
   analyzing the water quality data for the plurality of reclamation switch time levels to obtain the best reclamation switch time,
   wherein the waste water is to be discarded before reaching the reclamation switch time and to be reclaimed after reaching the reclamation switch time.

14. The method of claim 13 wherein the water quality data is analyzed by a computer to produce a plurality of water quality curves of the waste water, each water quality curve corresponding to one of the reclamation switch time levels.

15. The method of claim 14 wherein a parameter of the waste water quality to be detected comprises conductivity of the waste water.

16. The method of claim 15 wherein the waste water is directed to a water reclamation system during a reclamation period after each of the plurality of reclamation switch time levels, and wherein the best reclamation switch time is determined by selecting the lowest reclamation switch time level at which the conductivity of the waste water directed to the water reclamation system is generally below a preset limit.

17. The method of claim 16 wherein the preset limit is about 1000 µs/cm.

18. The method of claim 16 wherein the best reclamation switch time is determined by selecting the lowest reclamation switch time level at which the conductivity of the waste water is below the preset limit over at least about 90% of the reclamation time period.

19. The method of claim 18 wherein the conductivity of the waste water is below the preset limit over at least about 95% of the reclamation time period.

20. The method of claim 13 wherein the rinse recipe is selected from the group consisting of a quick-dump rinse recipe, an overflow rinse recipe, and a final-rinse recipe.

* * * * *